(12) United States Patent
Kvarnstrom et al.

(10) Patent No.: US 6,306,143 B1
(45) Date of Patent: *Oct. 23, 2001

(54) DISTRACTION OSTEOGENESIS FIXTURE

(75) Inventors: Bjarne Kvarnstrom, Huntington Beach, VA (US); Scott Lipka; Michael Luft, both of Peru, IL (US); Michael Block, Metarie, LA (US)

(73) Assignee: Nobel Biocere AB (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/232,731

(22) Filed: Jan. 19, 1999

(51) Int. Cl.$^7$ ................................................. A61B 17/58
(52) U.S. Cl. ............................................................ 606/105
(58) Field of Search .................................. 606/63, 65, 66, 606/73, 90, 105; 433/172, 173, 174, 176

(56) References Cited

U.S. PATENT DOCUMENTS

| | | | |
|---|---|---|---|
| 5,527,182 | * 6/1996 | Willougby | 433/172 |
| 5,584,629 | * 12/1996 | Bailey et al. | 606/73 |
| 5,601,429 | * 2/1997 | Blacklock | 433/174 |
| 5,899,940 | 5/1999 | Carchidi et al. | |
| 5,961,329 | * 10/1999 | Stucki-McCormick | 433/173 |
| 5,976,142 | * 11/1999 | Chin | 606/73 |

* cited by examiner

*Primary Examiner*—Jeffrey A. Smith
*Assistant Examiner*—Eduardo C. Robert
(74) *Attorney, Agent, or Firm*—Connolly Bove Lodge & Hutz, LLP

(57) ABSTRACT

A distraction osteogenesis fixture to be anchored in a bone, including a lower anchor, a translational screw, and an upper anchor. At least a portion of the lower anchor is externally threaded. At least a portion of the lower anchor includes an anti-rotational feature. The lower anchor includes an internal passage. At least a portion of the internal passage is threaded. At least a portion of the translational screw is externally threaded such that the translational screw is receivable by the threaded internal passage of the lower anchor. The upper anchor includes an internal passage for receiving a portion of the lower anchor and has an anti-rotational feature for engaging the anti-rotational feature of the lower anchor. The internal passage of the upper anchor includes a surface for engaging the translational screw. At least a portion of the upper anchor is externally threaded.

16 Claims, 13 Drawing Sheets

DISTRACTION OSTEOGENESIS FIXTURE

FIELD OF THE INVENTION

The invention relates to a method and device for increasing bone size or mass. In particular, the present invention relates to a method and apparatus for distraction osteogenesis. The present invention especially relates to increasing size of a portion of a patient's jawbone.

BACKGROUND OF THE INVENTION

In the context of certain medical and dental procedures, it may be desirable to increase the volume of bone at certain locations. The desire to increase bone volume may arise from a desire to strengthen a weak area in a bone. Another reason for increasing bone volume is to provide sufficient volume to accommodate a device implanted into the bone.

One method for increasing bone volume involves removing bone from one part of the body and transplanting to the area where it is desired to increase the bone volume. Bone implant procedures involve major surgery and disruption to the patient's body, wherein a patient's body is opened. Bone to be transplanted is then physically removed from a bone with saws and/or chisels, for example. One area where bone is often removed from is the ribs, another is the hip. The area that the bone is to be transplanted to is then cut open and a proper site prepared for receiving the transplanted bone. The transplanted bone is then transferred to the site. Bone transplant typically involves major surgery involving full anesthesia.

An alternative to bone implant surgery for increasing bone volume involves a process known as distraction osteogenesis. In distraction csteogenesis procedures, bone is stretched. Typically, an incision is made between two portions of bone and the portions of bone are then slowly separated from each other. It is desired that the space created by a separation of the bone portions is then filled in by new bone.

SUMMARY OF THE INVENTION

The present invention provides a distraction osteogenesis fixture. The fixture includes a lower anchor to be anchored in a jawbone. At least a portion of the lower anchor is externally threaded. Additionally, at least a portion of the lower anchor includes an anti-rotational feature. The lower anchor also includes an internal passage. At least a portion of the internal passage is threaded. The fixture also includes a translational screw. At least a portion of the translational screw is externally threaded such that the translational screw is receivable via threaded internal passage of the lower anchor. The fixture further includes an upper anchor having an internal passage for receiving a portion of the lower anchor and has an anti-rotational feature for engaging the anti-rotational feature of the lower anchor. The internal passage of the upper anchor includes a surface for engaging the translational screw. At least a portion of the upper anchor is externally threaded.

The present invention also provides a distraction osteogenesis method. The method includes forming a hole in a bone of a patient. The distraction osteogenesis fixture, including a lower anchor, an upper anchor, and a translational screw, is inserted into the hole. The lower anchor includes an externally threaded portion, an anti-rotational feature, and a threaded internal passage. The translational screw of the distraction osteogenesis fixture is inserted into the threaded internal passage of the lower anchor. An upper anchor of the distraction osteogenesis fixture is attached over the anti-rotational feature of the lower anchor and over the translational screw. The upper anchor includes an internal passage for receiving a portion of the lower anchor and has an anti-rotational feature for engaging the anti-rotational feature of the lower anchor. The internal passage of the upper anchor includes a surface for engaging the translational screw. At least a portion of the upper anchor is externally threaded. At least the cortical portion of the bone is cut. The translational screw is then rotated so as to cause linear translational movement of the upper anchor relative to the lower anchor, whereby the bone surrounding the upper anchor is moved away from the bone surrounding the lower anchor.

Still other objects and advantages of the present invention will become readily apparent to those skilled in the art from the following detailed description, wherein there are shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the drawings and description are to be regarded as illustrative in nature and not as restrictive.

BRIEF DESCRIPTION OF THE DRAWINGS

The above-mentioned objects and advantages of the present invention will be more clearly understood when considered in conjunction with the accompanying drawings, in which.

DETAILED DESCRIPTION OF THE INVENTION

Distraction osteogenesis is a process whereby bone is stretched to increase bone volume. According to distraction osteogenesis processes, at least one portion of a bone is at least partially separated from the bone. The position of the portion is gradually altered with respect to the bone. Time is then provided for new bone to fill in the space between the portion and the overall bone.

Distraction osteogenesis is particularly useful in dental applications. In dental applications, a portion of a patient's jawbone will be at least partially severed from the overall jawbone. The jawbone segment may then be gradually separated from the rest of the jawbone. New bone then fills in the space between the segment and the jawbone. By increasing the volume of bone in the jawbone, additional area can be provided to anchor or at least more securely anchor dental implants. Distraction osteogenesis can also be used in dental applications simply to strengthen a location on the jawbone to increase the bone volume at that location even if implants are not to be secured in the jawbone at that location.

Typical devices utilized in distraction osteogenesis, especially in dental applications, include a device or fixture that is secured to exterior of the jawbone. On the other hand, the present invention provides a device for distraction osteogenesis that may be implanted into the bone. An advantage of the present invention is that at least a portion of the distraction osteogenesis fixture may be utilized in a dental implant application after carrying out the distraction osteogenesis process. Alternatively, the present invention may also be carried out utilizing a resorbable material such that the fixture of the invention is absorbed into the bone after the distraction osteogenesis process.

Figure 1:
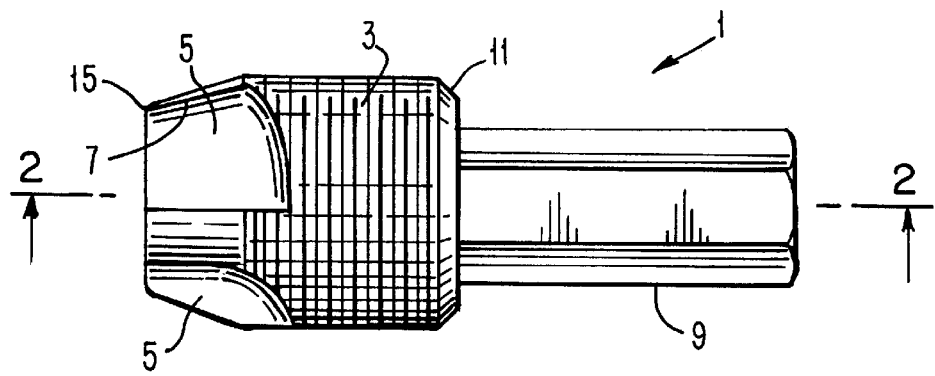
FIG. 1 represents a side plan view of an embodiment of a lower anchor of an embodiment of a distraction osteogenesis fixture according to the present invention.
Figure 2:
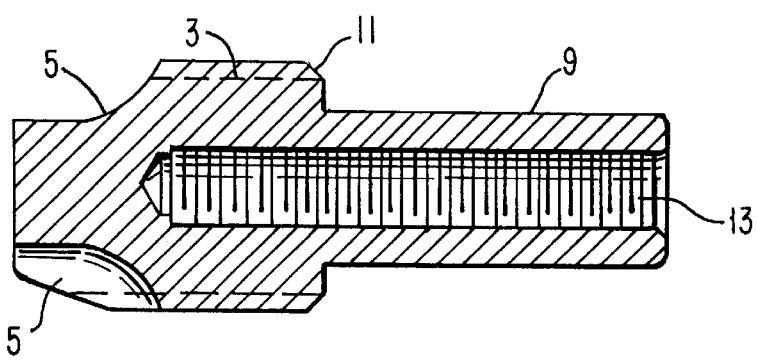
FIG. 2 represents a cross-sectional view of the embodiment of the lower anchor illustrated in FIG. 1 taken along the plane 2—2 illustrated in FIG. 1.
Figure 3:
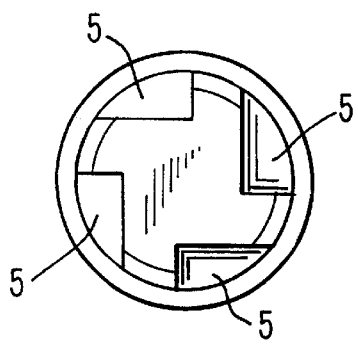
FIG. 3 represents a bottom plan view of the embodiment of the lower anchor illustrated in FIG. 1 and FIG. 2.
Figure 4:
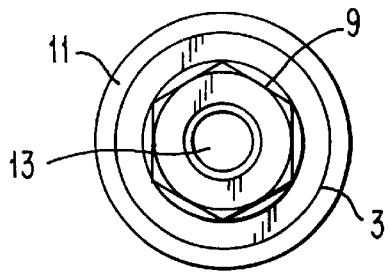
FIG. 4 represents a top plan view of the embodiment of the lower anchor illustrated in FIG. 1 and FIG. 2.
Figure 5:
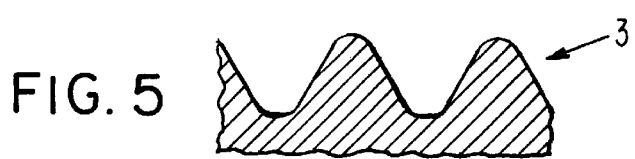
FIG. 5 represents a close-up cross-sectional view of a portion of an externally threaded portion of the lower anchor illustrated in FIG. 1 and FIG. 2.

According to one embodiment, a distraction osteogenesis fixture according to the present invention includes a lower anchor, a translation screw, and an upper anchor. FIG. 1 illustrates an embodiment of a lower anchor according to the present invention. At least a portion of the exterior surface of the lower anchor is threaded. The embodiment of the lower anchor 1 illustrated in FIG. 1 includes externally threaded portion 3.

The portion of the length of the lower and upper anchors that are externally threaded may vary depending upon the embodiment. It is the assembled lower and upper anchors, i.e. the osteogenesis fixture, that is screwed into a hole formed in the bone. Accordingly, typically, the length of the threaded portions of the lower and upper anchors according to the present invention is sufficient to help ensure that the fixture will be secured in the bone. Additionally, the characteristics, such as the dimensions and angles of the threads, may be varied from embodiment to embodiment to help ensure retention of the lower anchor in the bone. Typically, the externally threaded portion of the lower anchor includes right-hand threads.

To help facilitate insertion of the distraction osteogenesis fixture into a hole in a bone, the end of the lower anchor 1 to be inserted into the hole may include at least one scalloped flute 5. The embodiment illustrated in FIG. 1 includes four symmetrically scalloped flutes 5. The scalloped flutes may help to facilitate securing of the lower anchor into the hole in the bone by providing a volume for material in the hole or scraped from the side of the hole to be accommodated. The edges 7 of the scalloped flutes may also help to scrape away portions of the bone within the hole to facilitate insertion of the lower anchor.

The lower anchor may also include an anti-rotational feature. The anti-rotational feature may be accommodated on at least a portion of the lower anchor. The anti-rotational feature helps to prevent rotation of the lower anchor and other element(s) placed thereon relative to each other. For example, the anti-rotational feature may help to prevent relative rotation of the lower anchor and an upper anchor placed thereon, as described in greater detail below.

In the embodiment illustrated in FIG. 1, the anti-rotational feature includes a shaft 9 having a hexagonal cross-sectional shape. If the anti-rotational feature includes a shaft having a particular cross-sectional shape, the length of the shaft that includes the particular cross-sectional shape may vary depending upon a number of factors. For example, the distance or separation to be created by the distraction osteogenesis may determine the length of the shaft including the anti-rotational feature. Preferably, the length and cross-sectional area of a shaft that includes an anti-rotational feature is sufficient to prevent deformation of the shaft during movements of the distraction osteogenesis fixture according to the present invention.

If the anti-rotational feature includes a shaft having a particular cross-sectional shape on the lower anchor, the cross-sectional shape may vary. For example, rather than being a hexagon, the cross-sectional shape could be square or octagonal or any other desired shape. Additionally, it is not necessary that the anti-rotational feature include a shaft on the lower anchor engaged by a correspondingly shaped passage in the upper anchor. Other anti-rotational features may be utilized. One of ordinary skill in the art would be able to determine an appropriate anti-rotational feature once aware of the disclosure contained herein.

The lower anchor of the distraction osteogenesis fixture according to the present invention may also include an internal passage. At least a portion of the internal passage may be threaded. As seen in the embodiment illustrated in FIG. 1, the externally threaded portion of the lower anchor may have a greater diameter or cross-sectional area than a shaft including an anti-rotational feature.

The relative portions of the lower anchor that are externally threaded and that include an anti-rotational feature may vary depending upon the embodiment. According to one embodiment, more than one-half of the length of the lower anchor includes an anti-rotational feature. The externally threaded portion of the lower anchor may represent less than one-half of the length of the lower anchor. By including an anti-rotational feature that includes a shaft such as shaft 9 illustrated in FIG. 1 wherein the shaft has a smaller diameter than the externally threaded portion, the intersection 11 between the shaft and the externally threaded portion may act as a stop for limiting and providing a stop for the upper anchor when it is assembled on the lower anchor.

Internal passage 13 in the embodiment of the lower anchor illustrated in FIGS. 1–4 may accommodate a translational screw as described below in greater detail. In the distraction osteogenesis fixture according to the present invention, the threads of the internal passage 13, or any threaded portions of any portion of the distraction osteogenesis fixture, may be left handed or right handed. Although it may be desirable for certain threaded portions to have a handedness opposite from other threaded portions. The depth of the internal passage 13 of the lower anchor may vary depending upon the amount of separation between the bone segment and the bone that it is desired to create.

According to one example of a lower anchor according to the present invention, the length of the anchor from end to end is about 13.25 mm, ± about 0.2 mm. The length of the shaft 9 including the anti-rotational feature may be about 7 mm. The width of the externally threaded portion, measured from the roots of the threads may be about 4.25 mm. The tip 15 of the lower anchor 1 to be inserted into the hole in the bone may be about 3.7 mm at its base. Each scalloped flute may have a length of about 3 mm. Additionally, the width of the anti-rotational shaft, taken between parallel sides of the hexagon may be about 2.72 mm. According to one embodiment, the depth of the internal passage of the lower anchor is about 11.5 mm. This passage may include a threaded portion of about 10 mm. The external threads on the lower anchor may have crests spaced about 0.6 mm apart while the angle of the threads may be about 60°. Of course, the above dimensions only represent example of a lower anchor according to the present invention. The dimensions may change based upon the application.

Figure 6:
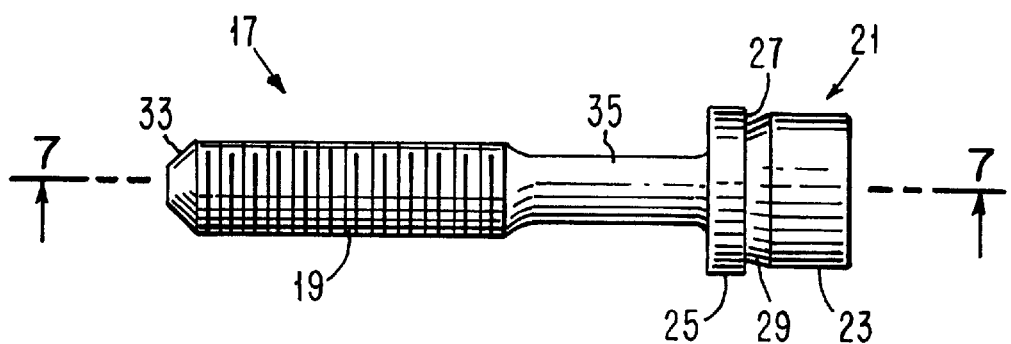
FIG. 6 represents a side plan view of an embodiment of a translational screw according to an embodiment of a distraction osteogenesis fixture according to the present invention.

The present invention also includes a translational screw. FIG. 6 illustrates an embodiment of a translational screw 17. At least a portion of the external surface of the translational screw is threaded so that at least the externally threaded portion of the translational screw is receivable via the threaded internal passage of the lower anchor. Accordingly, the external threads of the translational screw may be complimentary to the internal threads of the internal passage of the lower anchor. Along these lines, if the internal threads of the lower anchor are left handed, then the external threads of the translational screw should be left handed. The embodiment of the translational screw 17 illustrated in FIG. 6 includes an externally threaded portion 19.

The translational screw may include a surface for engaging a surface of an upper anchor as described below in greater detail. The exact form of the inter engaging surfaces of the translational screw in the upper anchor may vary, depending upon the embodiment. The embodiment of the translational screw illustrated in FIG. 6 includes a first or upper and regions of differing diameters in the vicinity of an end 21 of the translational screw opposite the end that the external threads are provided in the vicinity of.

The embodiment of the translational screw according to the present invention illustrated in FIG. 6 includes a region of a first diameter 23 closest to the end 21. This embodiment of the translational screw also includes a region having a second diameter 25 having a greater diameter than region 23. Region 25 is arranged on the translational screw at a greater distance from the end 21 than region 23.

Regions 23 and 25 of different diameters may be joined by a step 27. It is the surface of step 27 that may engage a surface of upper anchor to apply force to the upper anchor to result in lateral translational movement of upper anchor relative to the lower anchor The regions 23 and 25 may have cylindrical cross-sections. As a result, step 27 may have an annular shape. Step 27 and region 25 may be interconnected with region 23 by a frustoconical region 29. Region 29 may facilitate manufacture of the screw by helping, for example, to make the a cleaner cut and eliminate metal chips that otherwise could disturb the surface of step 27.

The translational screw may also include a region of reduced diameter 35 extending between the externally threaded portion 19 and the upper anchor engaging portions 23 and 25.

The translational screw may also include an internal passage 31, as in the embodiment illustrated in FIG. 6. At least a portion of the internal passage 31 may be threaded. The threaded internal passage of the translational screw may receive, among other things, a retaining screw, and a healing cap. The threads of the internal passage of the translational screw may be right handed or left handed. Typically, the handedness of the threads of the internal passage of the translational screw of the present invention is opposite as compared to the external threads of the translational screw.

The length and dimensions of the threads of the external threads of the translational screw may depend upon the desired degree of lateral translational movement of the translational screw with respect to the lower anchor that it is desired the distraction osteogenesis fixture permit.

According to one embodiment of a translational screw according to the present invention, the overall length of the translational screw is about 10.5 mm. The threaded portion of the exterior of the translational screw is about 5.5mm ± about 0.5 mm. The tip 33 of the translational screw may be beveled. The beveling may be about 45° with respect to the major axis of the translational screw. Typically, the bevel on the tip 33 of the translational screw matches a correspondingly angled bevel at the base of the internal passage of the lower anchor. The region of reduced diameter 23 may have a length at least of about 1.65 mm. If the frustoconical region 29 is included, the length of the upper anchor engaging portion having a reduced diameter has a length of about 1.85 mm. On the other hand, the length of the region 25 having a larger diameter than region 23 may be about 0.65 mm. The difference in diameters of these two regions may be about 0.2 mm.

Figure 10:
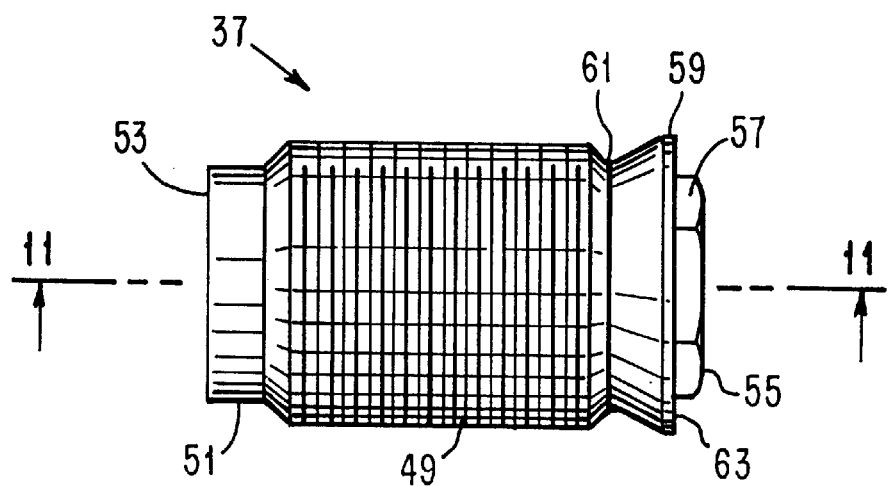
FIG. 10 represents a side plan of an embodiment of an upper anchor of an embodiment of a distraction osteogenesis fixture according to the present invention.

A distraction osteogenesis fixture according to the present invention also includes an upper anchor. FIG. 10 illustrates an embodiment 37 of an upper anchor according to the present invention. The upper anchor engages the lower anchor and the translational screw as described herein.

Figure 11:
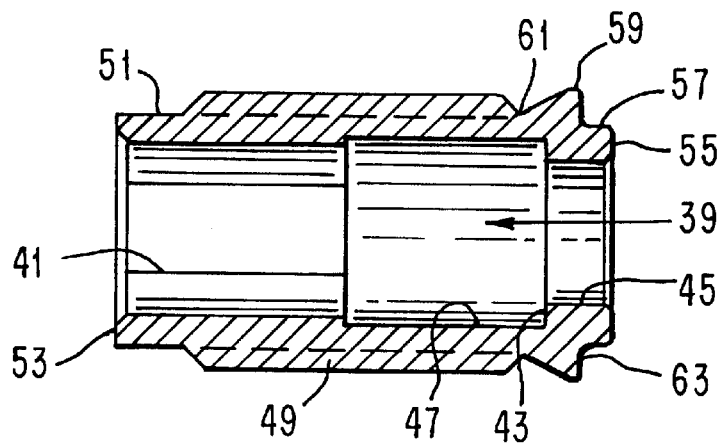
FIG. 11 represents a cross-sectional view of the embodiment of the upper anchor illustrated in FIG. 10 taken along the plane 11—11 illustrated in FIG. 10.

The upper anchor illustrated in FIG. 11 includes an internal passage 39 for receiving a portion of the lower anchor. The internal passage 39 of the upper anchor includes an anti-rotational feature for engaging the anti-rotational feature of the lower anchor. Therefore, the structure of the anti-rotational feature of the upper anchor is interdependent upon the structure of the anti-rotational feature of the lower anchor.

The internal passage 39 of the upper anchor 37 illustrated in FIGS. 10 and 11 includes a portion that has a hexagonal cross-sectional shape complementary to the hexagonal cross-sectional shape of the anti-rotational feature of the lower anchor illustrated in FIG. 1. However, as described above, the anti-rotational feature may have any configuration that permits it to engage the anti-rotational feature of the lower anchor and thereby prevent rotation of the upper anchor relative to the lower anchor when the upper anchor and the lower anchor are engaged with each other. Typically, the cross-sectional area of the hexagonal shaped anti-rotational feature of the upper anchor is only slightly larger than the cross-sectional area of the hexagonal anti-rotational feature of the lower anchor so as to reduce play in the connection between the upper anchor and the lower anchor.

The portion of the internal passage 39 of the upper anchor taken up by the anti-rotational feature may vary depending upon the embodiment. In the embodiment of the upper anchor of the present invention illustrated in FIGS. 10 and 11, the hexagonal shaped anti-rotational feature takes up less than half of the entire length of the internal passage 39. However, the length of such an anti-rotational feature may depend upon the length of the anti-rotational feature on the lower anchor and the amount of translational movement of the upper anchor with respect to the lower anchor that is desired.

Figure 7:
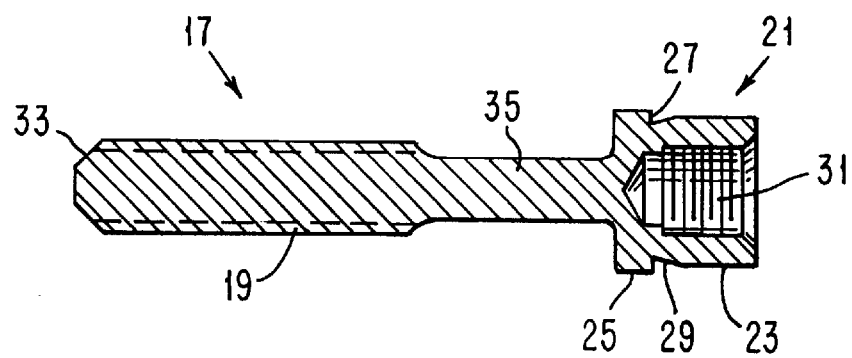
FIG. 7 represents a cross-sectional view of the embodiment of the translational screw illustrated in FIG. 6 taken along the plane 7—7 illustrated in FIG. 6.
Figure 8:
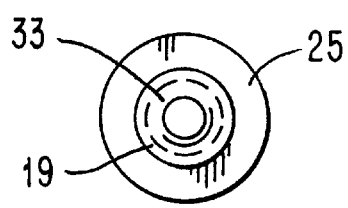
FIG. 8 represents a bottom plan view of the embodiment of the translational screw of the present invention illustrated in FIG. 6 and FIG. 7.
Figure 9:
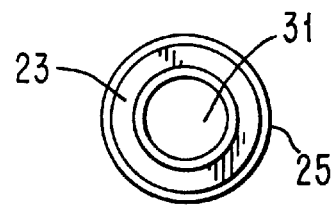
FIG. 9 represents a top plan of the translational screw illustrated in FIG. 6 and FIG. 7.

The internal passage 39 of the upper anchor may also include a surface for engaging the translational screw. In the embodiment of the translational screw of the present invention illustrated in FIG. 11, the inner passage 39 of upper anchor 37 includes translational screw-engaging surface 43. The embodiment of the upper anchor 37 illustrated in FIG. 11 is configured such that region of reduced diameter 23 of the translational screw illustrated in FIGS. 6 and 7 may be accommodated in the narrower opening 45 of internal passage 39.

According to the present invention, region 47 of the internal passage 39 of the upper anchor 37 may have a wider diameter to accommodate region 25 of wider diameter of the translational screw 17. The step 27 between the regions 25 and 23 of the translational screw may abut surface 43 in the internal passage 39 of the upper anchor 37 upon arranging the upper anchor over the lower anchor and the translational screw. Contact between these two surfaces facilitates translational movement of the upper anchor relative to the lower anchor as described below in greater detail.

At least a portion of the outer surface of the upper anchor may be threaded. The threaded portion of the exterior surface of the upper anchor may engage bone forming the sidewalls of a hole made in a bone. Typically, the external threads on the upper anchor are right handed. Typically, the exterior threads on the upper anchor have the same handedness as the exterior threads on the lower anchor.

Figure 31:
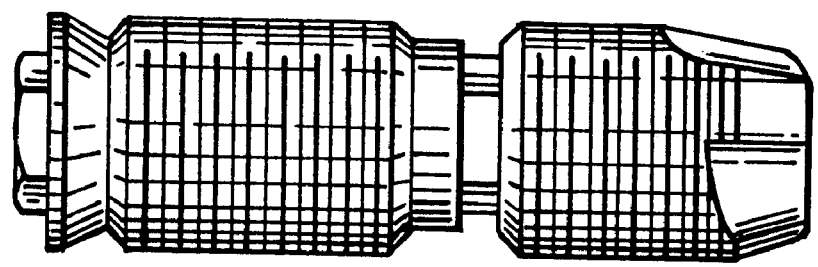
FIG. 31 represents a side plan view of an embodiment of a fully assembled distraction osteogenesis fixture according to the present invention.

The upper anchor may also include an indicator for indicating the position of the upper anchor relative to the lower anchor, particularly when the lower anchor is fully inserted into the upper anchor. In the embodiment illustrated in FIGS. 10 and 11, the indicator includes a region 51 having a reduced diameter as compared to the externally threaded portion 49. The region of reduced diameter may be arranged in the vicinity of the end 53 of the upper anchor 37 for receiving the lower anchor 1. As illustrated in FIG. 31, when a distraction osteogenesis fixture according to the present invention is assembled, if the upper anchor includes such a region of reduced diameter, it forms a band where the end 53 of the upper anchor abuts against the surface 11 of the lower anchor 1. This reduced diameter or other indicator may help to determine the location of the end 53 of the upper anchor of the fixture during the distraction osteogenesis process as well.

The end 55 of the upper anchor opposite the end 53 for receiving the lower anchor may include an external anti-rotational feature. The embodiment of the upper anchor illustrated in FIGS. 10 and 11 includes a region 57 having a hexagonal cross-sectional shape. This anti-rotational feature may function to engage, among other things, a fixture mount. This external anti-rotational feature of the upper anchor may be useful when the distraction osteogenesis according to the present invention is to remain in place and be utilized in tooth implant applications. Of course the anti-rotational feature may have configurations other than a hexagonal shape.

The upper anchor 37 may also include a flange 59. Flange 59 may be a region having a diameter greater than the diameter of the anti-rotational feature. The flange may abut against a fixture mount or other element applied over the external anti-rotational feature of the upper anchor. The upper anchor according to the present invention may also include a reduced diameter collar region 61 between the flange 59 and the externally threaded portion 49.

Figure 12:
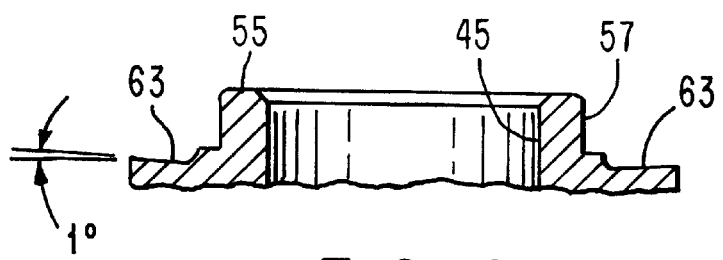
FIG. 12 represents a close-up cross-sectional view of an end of the embodiment of the upper anchor illustrated in FIG. 10 taken along the line 12—12 in FIG. 13.
Figure 13:
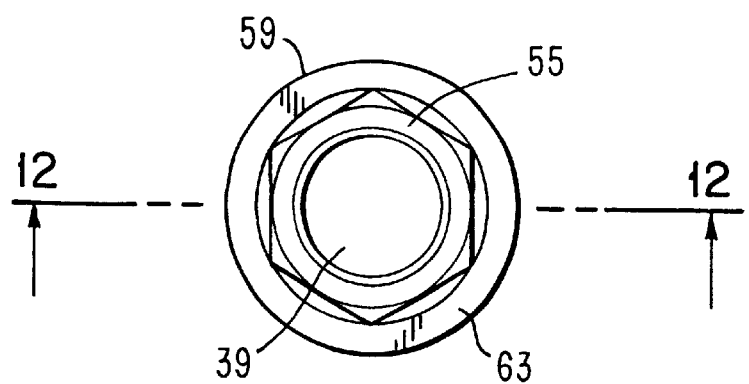
FIG. 13 represents a bottom end plan view of the embodiment of the upper anchor illustrated in FIG. 10.
Figure 14:
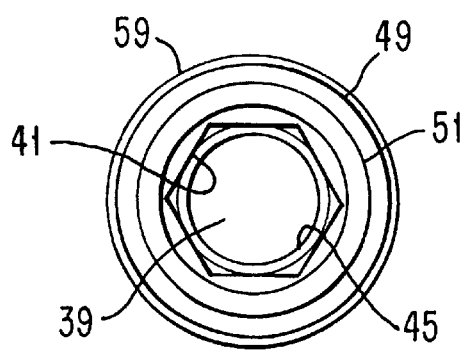
FIG. 14 represents a top plan view of the embodiment of the upper anchor illustrated in FIG. 10.
Figure 15:
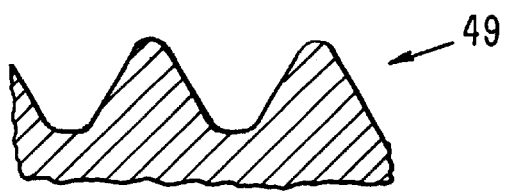
FIG. 15 represents a close-up cross-sectional view of a portion of a threaded exterior portion of the embodiment of the upper anchor illustrated in FIG. 10.

As illustrated in the close up cross-sectional view shown in FIG. 12, according to the present invention, opening of internal passage 39 at the end 55 of the upper fixture 37 may be beveled. Additionally, the exterior surface of the upper anchor where the anti-rotational feature 57 intersects with flange 59 may be stepped. Surface 63 of flange 59 may be angled about 1° away from end 55 with increasing distance toward the center axis of upper anchor 37. According to the present invention, opening of internal passage 39 at end 55 of upper anchor 37 may also be beveled.

The present invention may also include a depth gauge. The depth gauge may be utilized to indicate the region where the bone should be cut during the distraction osteogenesis process as described below in greater detail. Accordingly, the depth gauge may be used to indicate the location where the end 53 of upper anchor 37 abuts against surface 11 of lower anchor 1. It is important to know the location of this surface since after securing the distraction osteogenesis fixture of the present invention in the bone of a patient, prior to beginning the bone stretching process, the bone stretching process will begin at the point where the upper anchor becomes separated from the lower anchor. In the embodiment of the present invention illustrated in the drawings, this will begin to occur in the vicinity of the end of the externally threaded portion of the upper anchor, which is indicated by the indicator as described above.

Figure 16:
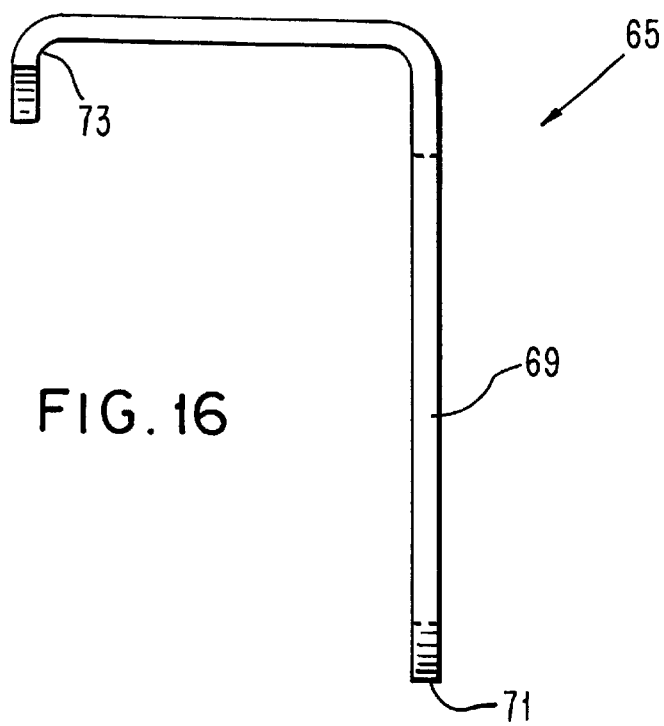
FIG. 16 represents a cross-sectional view of an embodiment of a depth gauge that may be utilized with a distraction osteogenesis fixture according to the present invention.
Figure 17:
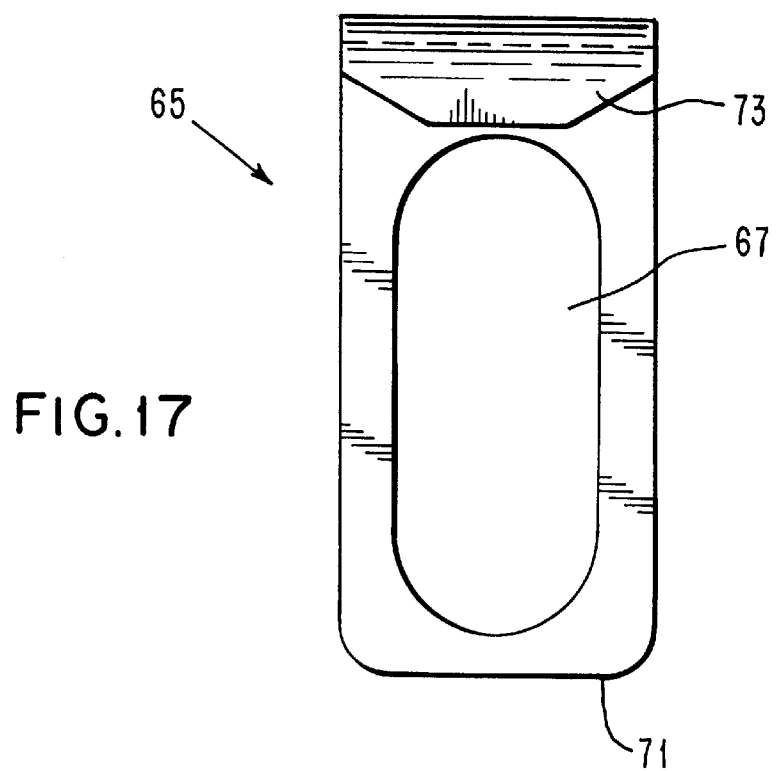
FIG. 17 represents a top view of the embodiment of the depth gauge illustrated in FIG. 16.

FIGS. 16 and 17 illustrate an embodiment 65 of a depth gauge according to the present invention. Depth gauge 65 may include slot 67 for receiving the anti-rotational feature 57 of the upper anchor 37 therein. Slot 67 may be elongated as illustrated in FIG. 17 to permit the depth gauge to slide along the anti-rotational feature of the upper anchor, thereby accommodating various thicknesses of bone where the fixture according to the present invention is installed. The short arm 73 of the depth gauge 65 may have a position such that when depth gauge is arranged on the upper anchor 37, it will indicate the position the base 53 of the upper anchor 37. The short arm 73 indicates the apical-occlusal position of the base 53 of the upper anchor 37.

The present invention may also include a retaining screw. The retaining screw may be inserted in the inner passage of translational screw 17 for helping to immobilize the upper anchor relative to the translational screw. The retaining screw may also help to provide means for rotating the translational screw to cause translational movement of the upper anchor relative to the lower anchor.

Figure 18:
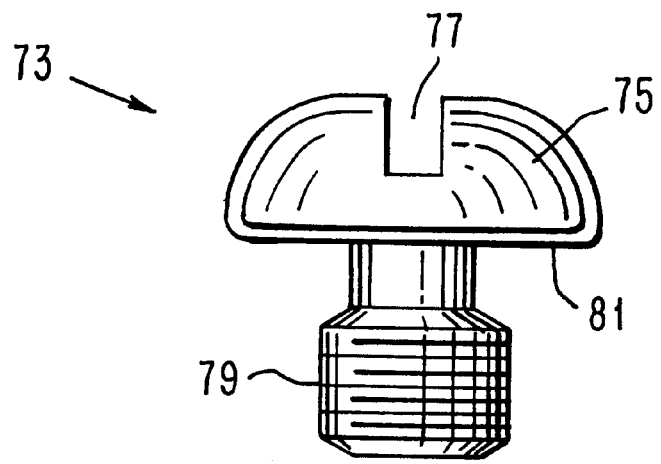
FIG. 18 represents a side view of an embodiment of a retaining screw of an embodiment of a distraction osteogenesis fixture according to the present invention.
Figure 19:
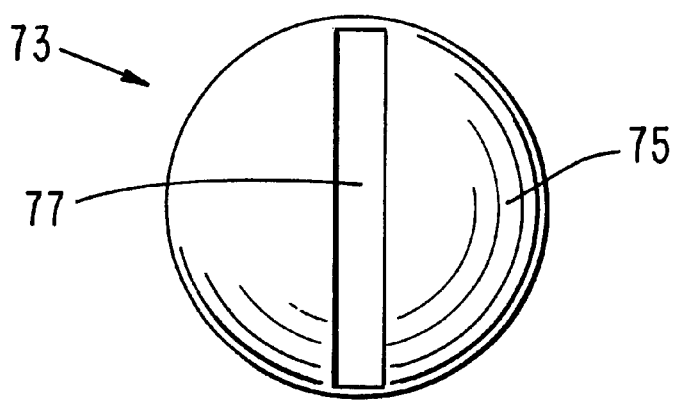
FIG. 19 represents a top plan view of the embodiment of the retaining screw illustrated in FIG. 18.

FIGS. 18 and 19 illustrate an embodiment of a retaining screw according to the present invention. The embodiment of the retaining screw 73 illustrated in FIGS. 18 and 19 includes a screw head 75. The screw head 75 includes slot 77 for engaging in mechanical or motor driven screw driver for rotating the retaining screw.

The retaining screw according to the present invention may also include an externally threaded shaft 79. The handedness of the threads on the externally threaded shaft 79 of retaining screw 73 match the handedness of the threads on the internally threaded passage 31 of retaining screw 17. According to one embodiment of the present invention, the threads on the externally threaded portion of the retaining screw and the threads on the internal passage of the translational screw 17 are right handed. According to such an embodiment, the external threads on the translational screw are left handed. Also according to this embodiment, when retaining screw is fully inserted in the translational screw and retaining screw is further rotated in a direction that would tighten the retaining screw in the translational screw internal passage, due to the opposite handedness of the external threads on the translational screw, translational screw will unscrew from the lower anchor thereby resulting in the translational movement of the upper anchor with respect to the lower anchor.

Typically, the head 75 of retaining screw 73 has a larger diameter than the diameter of the opening of the upper anchor that the section 23 of reduced diameter of the translational screw extends through. In this manner, the surface 81 of retaining screw cap 75 that contacts the upper surface of the upper anchor and the step 27 of translational screw contacting the surface 43 of the upper anchor may serve to immobilize the upper anchor translational screw and retaining screw with respect to each other when the retaining screw is fully inserted into the inner passage in the translational screw and tightened therein.

The present invention may also include a healing cap for helping to seal the opening of the distraction osteogenesis fixture of the present invention after implantation into a bone. A healing cap according to the present invention may include one or two pieces. Regardless of whether the healing cap includes one or two pieces, the healing cap typically includes a threaded shaft for insertion into the threaded internal passage of the translational screw as well as a portion that engages an upper surface of the upper anchor.

FIGS. 20–24 illustrate an embodiment of a two piece healing cap according to the present invention. This embodiment includes a cap screw portion and a cap portion. The cap screw portion engages the internally threaded passage of the translational screw.

Figure 20:
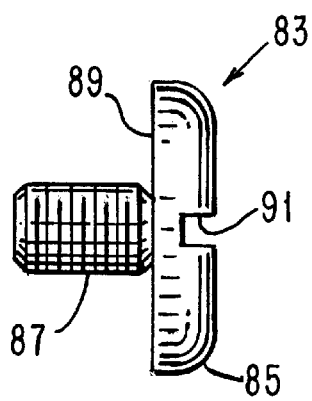
FIG. 20 represents a side view of an embodiment of a cap screw portion of an embodiment of a two piece healing cap of an embodiment of a distraction osteogenesis fixture according to the present invention.
Figure 21:
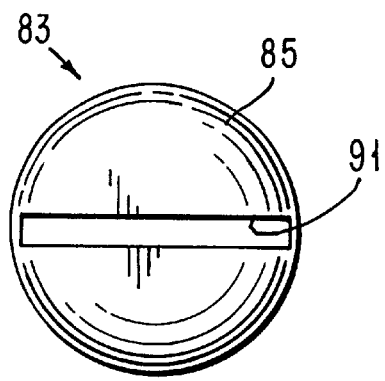
FIG. 21 represents a top plan view of the embodiment of the cap screw illustrated in FIG. 20.

FIG. 20 illustrates a side plan view of the cap screw 83 of the two piece healing cap according to the present invention. Cap screw 83 includes cap portion 85 and threaded shaft portion 87. As stated above, threaded shaft portion is receivable by threaded internal passage 31 of translational screw 17. Accordingly, the handedness of the threads of healing cap screw 87 preferably are complementary to the handedness of the threads of internal passage 31 of translational screw 17.

Figure 22:
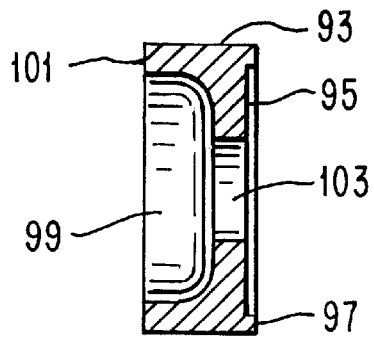
FIG. 22 represents a cross-sectional view of an embodiment of a cylinder of an embodiment of a two piece healing cap of an embodiment of a distraction osteogenesis fixture according to the present invention.
Figure 23:
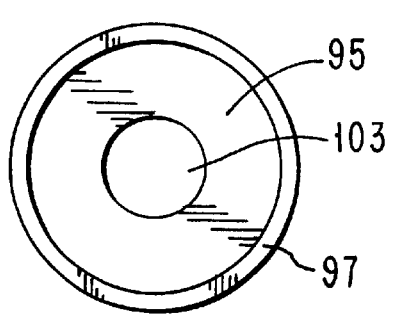
FIG. 23 represents a bottom plan view of the embodiment of the healing cap cylinder illustrated in FIG. 22.
Figure 24:
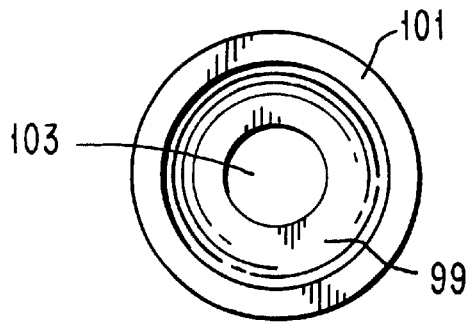
FIG. 24 represents a top plan of the embodiment of the healing cap cylinder illustrated in FIG. 22.

Typically, cap portion 85 has a width larger than the width of a passage in a healing cap portion illustrated in FIGS. 22–24. Engagement of surface 89 of cap portion 85 with surface 95 of cylindrical portion 93, described below in greater detail, of the two piece healing cap helps to seal the opening of the cylinder portion, in turn, the upper anchor. Cap screw portion 83 may also include a slot 91 for engaging a manual or motor operated screw driver.

The two piece healing cap illustrated in FIGS. 20–24 also includes cylinder portion 93 illustrated in FIGS. 22–24. Cylinder portion 93 may include cap screw engaging surface 95. The cap screw engaging surface may be recessed in the top surface 97 of cylinder portion 93 as in the embodiment illustrated in FIG. 22. This may help to ensure that the healing cap seals the distraction osteogenesis fixture according to the present invention.

The embodiment of the healing cap cylinder portion 93 illustrated in FIGS. 20–24 may also include a recess 99 for receiving top portion 57 of the upper anchor 37. Surface 101 of two piece healing cylinder portion 93 may engage the surface of the flange 59 of the upper anchor to seal the upper anchor. Cap screw portion 83 may be received by passage 103 in the cylinder portion 93.

Figure 28:
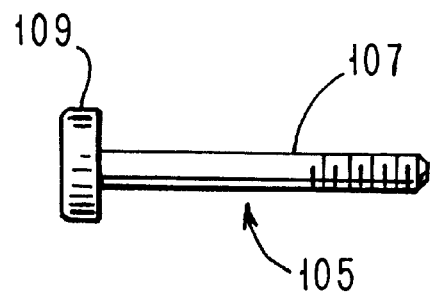
FIG. 28 represents a side plan of an embodiment of a fixture mount cap screw according to an embodiment of a distraction osteogenesis fixture according to the present invention.
Figure 29:
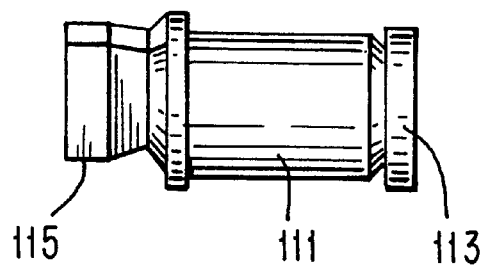
FIG. 29 represents a side plan view of a cylinder of an embodiment of a fixture mount according to an embodiment of a distraction osteogenesis fixture according to the present invention.

The present invention may also include a fixture mount for inserting the distraction osteogenesis fixture into the bone. FIGS. 28 and 29 illustrate an example of an embodiment of a fixture mount according to the present invention. A fixture mount according to the present invention may include two elements. The two elements include a fixture mount screw cap 105 and a fixture mount 111. The screw cap has a threaded end 107 and a head 109. One element of the fixture mount may be cylindrically shaped. The cylinder may include an internal passage.

One end 113 of the internal passage of the cylinder portion of the embodiment of the fixture mount illustrated in FIGS. 28 and 29 may include a hexagonally-shaped opening to engage the hexagonal shaped external anti-rotational feature on the upper anchor. The opening of the fixture mount may include a structure to engage the anti-rotational feature on the upper anchor. The end of the cylinder opposite the end 115 that engages the upper anchor may include structure for engaging a manual or motorized torque transfer device for driving the distraction osteogenesis fixture into the bone by rotation.

Figure 25:
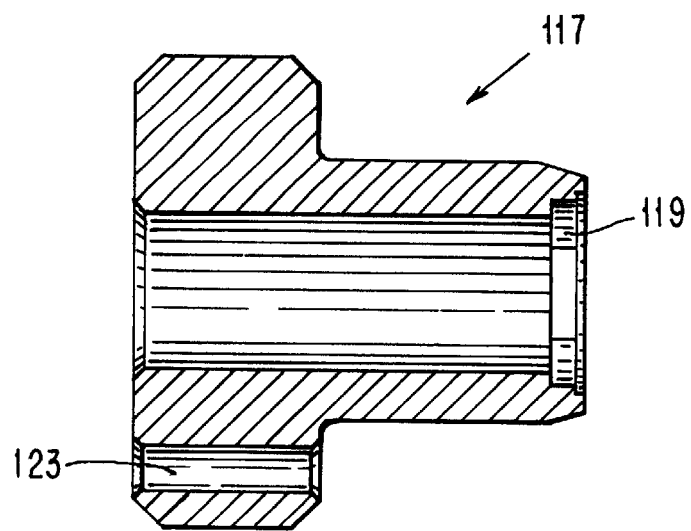
FIG. 25 illustrates a cross-sectional view of an embodiment of a manual fixture counter torque of an embodiment of a distraction osteogenesis fixture according to the present invention.
Figure 26:
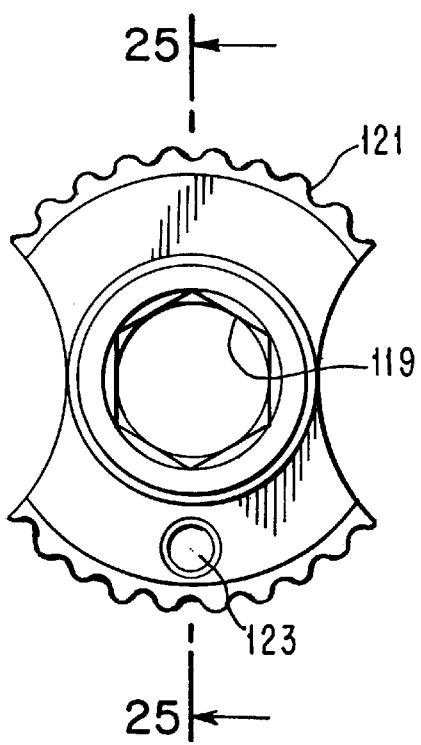
FIG. 26 illustrates a top plan view of the embodiment of the manual fixture counter torque illustrated in FIG. 25.
Figure 27:
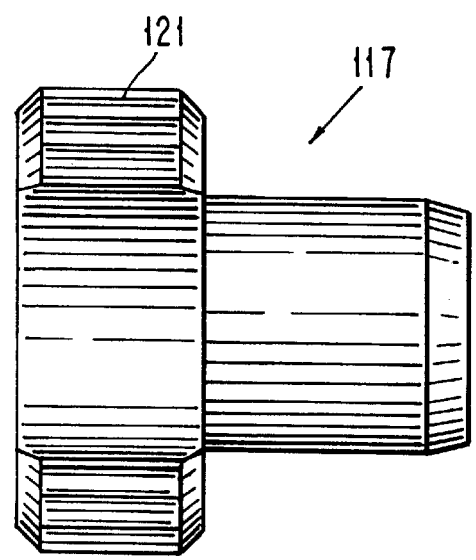
FIG. 27 illustrates a side plan view of the embodiment of the manual fixture counter torque illustrated in FIG. 25 and FIG. 26.

A distraction osteogenesis fixture according to the present invention may also include a manual fixture counter torque element. An embodiment of a manual fixture counter torque element according to the present invention is illustrated in FIGS. 25–27. The manual fixture counter torque element 117 includes an anti-rotational feature 119 for mating to the anti-rotational feature of the upper anchor.

The manual fixture counter torque element may also include features for applying torque to the element and as a result, the upper anchor of the distraction osteogenesis fixture. For example, as illustrated in the embodiment shown in FIG. 26, the manual fixture counter torque may include a textured handle region 121.

The manual fixture counter torque may also include a ligature hole 123. The ligature hole engages a suture, preventing the fixture counter torque element from accidental loss in the patient's throat.

Figure 30:
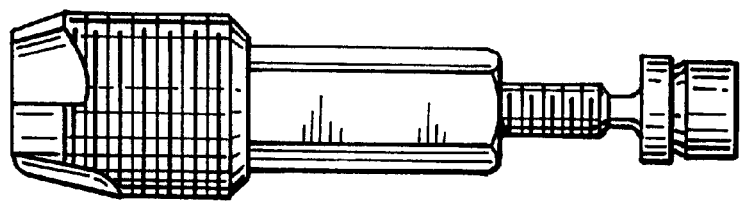
FIG. 30 represents a side plan view of an embodiment of a lower anchor and a translational screw according to a distraction osteogenesis fixture according to the present invention, when partially assembled.
Figure 32:
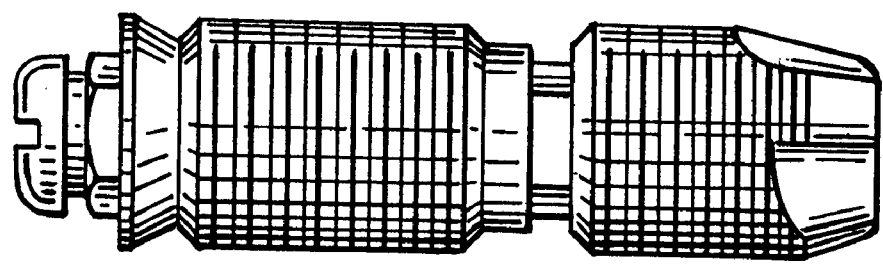
FIG. 32 represents a side plan view of the assembled distraction osteogenesis fixture according to the present invention also including a retaining screw.
Figure 33:
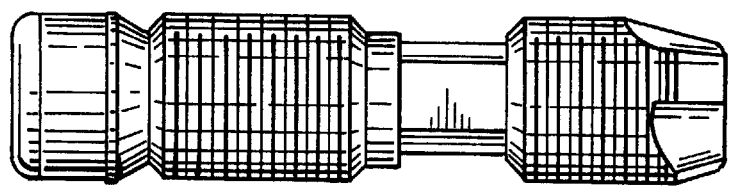
FIG. 33 represents a side plan view of the embodiment of the distraction osteogenesis fixture illustrated in FIG. 30, FIG. 31 and FIG. 32 also including a healing cap.
Figure 34:
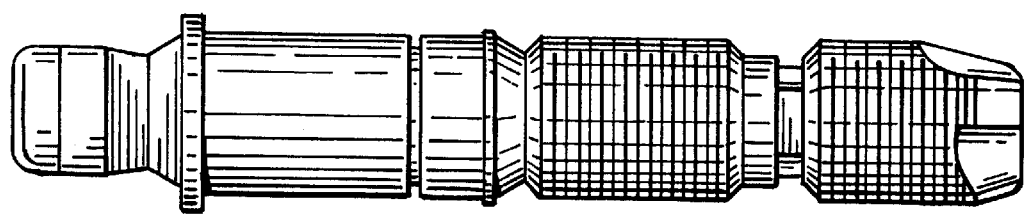
FIG. 34 represents a side plan view of an embodiment of a distraction osteogenesis fixture with an attached fixture mount.

FIGS. 30–34 illustrate assembly of a distraction osteogenesis fixture according to the present invention. Along these lines, FIG. 30 illustrates an embodiment of a distraction osteogenesis fixture according to the present invention showing assembly of the lower anchor and the translational screw. On the other hand, FIG. 31 illustrates a fully assembled distraction osteogenesis fixture including the upper anchor and lower anchor and translational screw. Additionally, FIG. 32 illustrates an embodiment of the distraction osteogenesis fixture according to the present invention wherein the retaining screw has been inserted into the translational screw and the upper anchor partially translated from the lower anchor. Furthermore, FIG. 33 illustrates an embodiment of the present invention including a healing cap connected to the upper anchor and translational screw wherein the upper anchor has been translated a distance on the lower anchor. Still further, FIG. 34 illustrates an example of a distraction osteogenesis fixture with a fixture mount attached to the upper anchor and translational screw.

Unlike distraction osteogenesis devices that are applied to the outer surface of the bone, the present invention is inserted inside the bone. A fixture according to the present invention may be made of a biocompatible material such as titanium. The fixture can be made for permanent installation. Along these lines, it is common after stretching for the fixture to be used as a normal dental implant screw with an abutment and prosthetic device attached, such as a tooth. On the other hand, the present invention may be made of a resorbable material so that after distraction osteogenesis, the distraction osteogenesis fixture is resorbed into the bone tissue.

The present invention also includes a distraction osteogenesis method. According to the method of the present invention, a hole may be formed in a bone of a patient. Typically, the present invention is utilized in dental applications. Therefore, the hole is formed in the jawbone in a patient.

Next, a distraction osteogenesis fixture, including a lower anchor, translational screw, an upper anchor may be inserted into the hole by screwing it into the hole. To facilitate the insertion of the distraction osteogenesis fixture into the hole formed in the bone, a fixture mount may be attached to the distraction osteogenesis fixture. The pre-assembled lower anchor, upper anchor and translational screw are screwed into the hole in the bone to the desired level. Next, the bone may be cut.

To facilitate cutting of the bone, a depth gauge as described above may be arranged on the upper anchor. Typically, the cortical bone only is then cut at the level where the end of the upper anchor abuts against the lower anchor. The depth gauge may help to determine the level at which the bone should be cut. In addition to horizontal cuts, vertical cuts may be made in the bone. In cutting bone, typically, only the cortical or hard portion of the bone is cut, leaving the softer, vascularized underlying bone portion, including nerves, intact.

After cutting the bone, the translational screw may be rotated to cause the upper anchor to move relative to the lower anchor. A retaining screw may be utilized as described above to assist in this process. The rate that the upper anchor may be moved relative to the lower anchor may vary depending upon the characteristics of the patient's bone. According to one embodiment of a method according to the present invention, the upper anchor is moved relative to the lower anchor about 1 mm per day. However, any desired rate may be employed. Along these lines, the rate that the upper anchor is moved relative to the lower anchor may be from about 0.5 mm to about 1 mm per day.

The fixtures may be moved more than once each day. Alternatively, more than one day may elapse between relative movements of the fixtures. The time period between relative movements of the fixtures may vary.

After the upper anchor is moved to the desired amount relative to the lower anchor, the distraction osteogenesis fixture according to the present invention may be permitted to sit stationary so that the spaces created by movement of the upper anchor relative to the lower anchor may be filled in with new bone. Typically this is accomplished in a period of about 90 to about 180 days. After sitting for sufficient time to permit bone to fill in the spaces created by the present invention, an abutment and prosthetic tooth or bridge may be affixed to the fixture of the present invention. Alternatively, the fixture according to the present invention will be resorbed into the bone.

Figure 35:
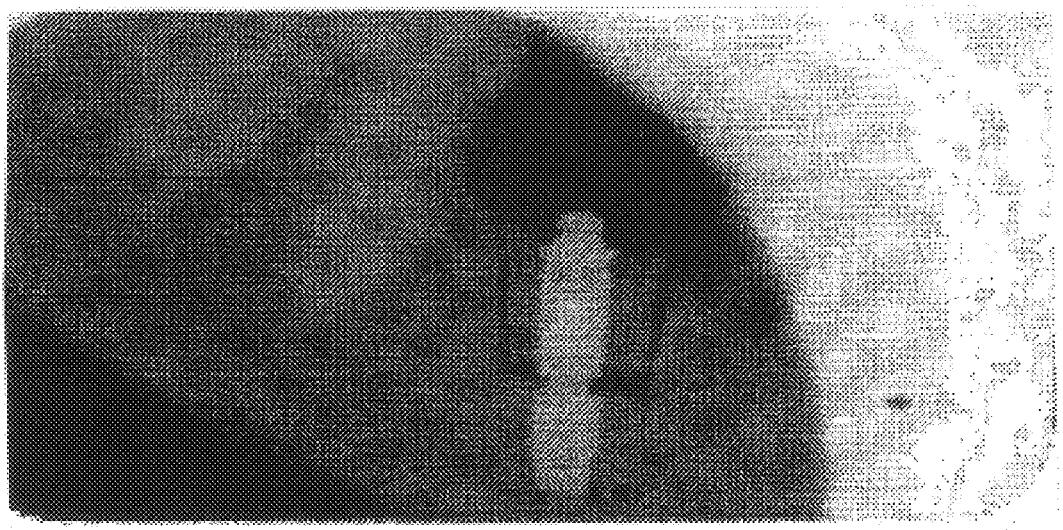
FIG. 35 represents an x-ray illustrating an embodiment of a distraction osteogenesis fixture implanted in a patient's jawbone wherein a piece of the jawbone has been separated from the patient's jawbone by about 0.5 mm.
Figure 36:
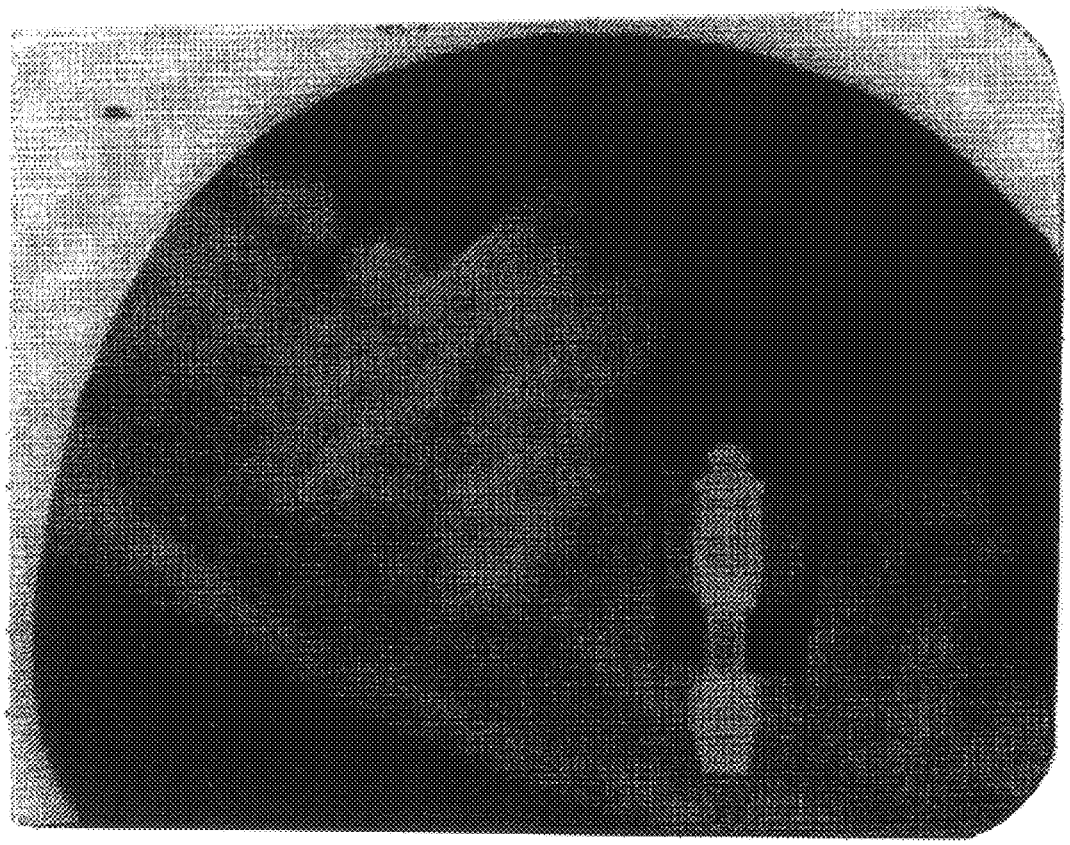
FIG. 36 represents an x-ray illustrating the fixture shown in FIG. 35 wherein the piece of the jawbone has been separated from the jawbone by about 4.5 mm.
Figure 37:
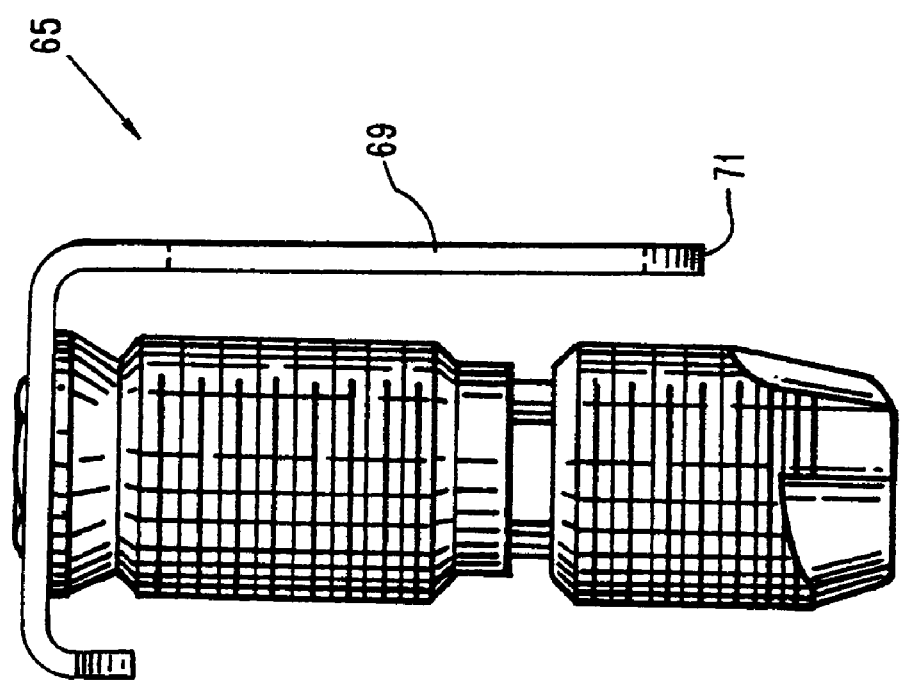
FIG. 37 illustrates a depth gauge attached to the upper anchor.

As stated above, the cortical bone may be cut, leaving bone marrow intact. FIGS. 35 and 36 provide x-ray images illustrating a fixture according to the present invention implanted in the jawbone of a patient. According to FIG. 35, the upper anchor has been moved about 0.5 mm with respect to the lower anchor. FIG. 36 provides an x-ray image illustrating the patient shown in FIG. 35 wherein the upper anchor has been moved a total of about 4.5 mm.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

We claim:

1. A distraction osteogenesis fixture, comprising:

a lower anchor to be anchored in a bone, at least a portion of the lower anchor including external bone-engaging threads, at least a portion of the lower anchor also including an anti-rotational feature, the lower anchor including an internal passage, at least a portion of the internal passage being threaded;

a translational screw, at least a portion of the translational screw being externally threaded such that the translational screw is receivable by the threaded internal passage of the lower anchor;

an upper anchor to be anchored in bone and including an internal passage for receiving a portion of the lower anchor and having an anti-rotational feature for engaging the anti-rotational feature of the lower anchor, the internal passage of the upper anchor including a surface for engaging the translational screw, at least a portion of the upper anchor including external bone-engaging threads; and wherein the translational screw further includes a threaded internal passage in the vicinity of a first end and wherein the externally threaded portion of the translational screw extends from in the vicinity of a second end.

2. The fixture according to claim 1, wherein the threads of the threaded internal passage are right-handed.

3. A distraction osteogenesis fixture, comprising:

a lower anchor to be anchored in a bone, at least a portion of the lower anchor including external bone-engaging threads, at least a portion of the lower anchor also including an anti-rotational feature, the lower anchor including an internal passage, at least a portion of the internal passage being threaded;

a translational screw, at least a portion of the translational screw being externally threaded such that the translational screw is receivable by the threaded internal passage of the lower anchor;

an upper anchor to be anchored in bone and including an internal passage for receiving a portion of the lower anchor and having an anti-rotational feature for engaging the anti-rotational feature of the lower anchor, the internal passage of the upper anchor including a surface for engaging the translational screw, at least a portion of the upper anchor including external bone-engaging threads;

wherein the translational screw further includes an external cylindrical surface in the vicinity of a first end, the external cylindrical surface including two regions having different diameters such that a step between the two regions engages the translational screw engaging surface of the upper anchor; and wherein the translational screw further includes a frusto-conical region arranged between the two different diameter regions.

4. A distraction osteogenesis fixture, comprising:

a lower anchor to be anchored in a bone, at least a portion of the lower anchor including external bone-engaging threads, at least a portion of the lower anchor also including an anti-rotational feature, the lower anchor including an internal passage, at least a portion of the internal passage being threaded;

a translational screw, at least a portion of the translational screw being externally threaded such that the translational screw is receivable by the threaded internal passage of the lower anchor;

an upper anchor to be anchored in bone and including an internal passage for receiving a portion of the lower anchor and having an anti-rotational feature for engaging the anti-rotational feature of the lower anchor, the internal passage of the upper anchor including a surface for engaging the translational screw, at least a portion of the upper anchor including external bone-engaging threads; and further comprising:

a retaining screw for retaining the upper anchor on the translational screw, wherein the translational screw includes an threaded internal passage for receiving the retaining screw, wherein the retaining screw fixes the upper anchor with respect to the translational screw.

5. The fixture according to claim 4, wherein the retaining screw and the translational screw threaded internal passage both have right-handed threads, such that after fixing of the upper anchor and the translational screw rotation of the retaining screw rotates the translational screw thereby causing displacement of the translational screw and the upper anchor relative to the lower anchor.

6. The fixture according to claim 4, wherein the retaining screw head has a diameter greater than a diameter of an opening of the internal passage of the upper anchor.

7. A distraction osteogenesis fixture, comprising:

a lower anchor to be anchored in a bone, at least a portion of the lower anchor including external bone-engaging threads, at least a portion of the lower anchor also including an anti-rotational feature, the lower anchor including an internal passage, at least a portion of the internal passage being threaded;

a translational screw, at least a portion of the translational screw being externally threaded such that the translational screw is receivable by the threaded internal passage of the lower anchor;

an upper anchor to be anchored in bone and including an internal passage for receiving a portion of the lower anchor and having an anti-rotational feature for engaging the anti-rotational feature of the lower anchor, the internal passage of the upper anchor including a surface for engaging the translational screw, at least a portion of the upper anchor including external bone-engaging threads; and further comprising:

a depth gauge attached to a first end of the upper end of the upper anchor for indicating a location of a second end of the upper anchor.

8. A distraction osteogenesis fixture, comprising:

a lower anchor to be anchored in a bone, at least a portion of the lower anchor including external bone-engaging threads, at least a portion of the lower anchor also including an anti-rotational feature, the lower anchor including an internal passage, at least a portion of the internal passage being threaded;

a translational screw, at least a portion of the translational screw being externally threaded such that the translational screw is receivable by the threaded internal passage of the lower anchor;

an upper anchor to be anchored in bone and including an internal passage for receiving a portion of the lower anchor and having an anti-rotational feature for engaging the anti-rotational feature of the lower anchor, the internal passage of the upper anchor including a surface for engaging the translational screw, at least a portion of the upper anchor including external bone-engaging threads; and further comprising:

a healing cap including an externally threaded shaft and a cap, wherein the translational screw includes a threaded internal passage for receiving the shaft of the healing cap.

9. The fixture according to claim 8, wherein the shaft of the healing cap and the threaded internal passage of the translational screw including right-handed threads.

10. The fixture according to claim 8, wherein the healing cap includes screw portion that includes the threaded shaft and a separate cylindrical portion including a passage for receiving the threaded shaft of the screw portion.

11. A distraction osteogenesis fixture, comprising:

a lower anchor to be anchored in a bone, at least a portion of the lower anchor including external bone-engaging threads, at least a portion of the lower anchor also including an anti-rotational feature, the lower anchor including an internal passage, at least a portion of the internal passage being threaded;

a translational screw, at least a portion of the translational screw being externally threaded such that the translational screw is receivable by the threaded internal passage of the lower anchor;

an upper anchor to be anchored in bone and including an internal passage for receiving a portion of the lower anchor and having an anti-rotational feature for engaging the anti-rotational feature of the lower anchor, the internal passage of the upper anchor including a surface for engaging the translational screw, at least a portion of the upper anchor including external bone-engaging threads; and further comprising:

a fixture mount including a threaded shaft, wherein the translational screw includes a threaded internal passage for receiving the shaft of the fixture mount, the fixture mount further including a fixture receiving member.

12. The fixture according to claim 11, wherein the threaded internal passage of the translational screw and the threaded shaft of the fixture mount include right-handed threads.

13. The fixture according to claim 11, wherein the upper anchor further includes an external anti-rotational feature, and the fixture mount further includes an internal anti-rotational feature for engaging the external anti-rotational feature of the upper anchor.

14. A distraction osteogenesis fixture, comprising:

a lower anchor to be anchored in a bone, at least a portion of the lower anchor including external bone-engaging threads, at least a portion of the lower anchor also including an anti-rotational feature, the lower anchor including an internal passage, at least a portion of the internal passage being threaded;

a translational screw, at least a portion of the translational screw being externally threaded such that the translational screw is receivable by the threaded internal passage of the lower anchor;

an upper anchor to be anchored in bone and including an internal passage for receiving a portion of the lower anchor and having an anti-rotational feature for engaging the anti-rotational feature of the lower anchor, the internal passage of the upper anchor including a surface for engaging the translational screw, at least a portion of the upper anchor including external bone-engaging threads; and further comprising:

a manual fixture counter torque member attached to the upper anchor and including at least one element for engaging an apparatus for applying torque to the fixture, wherein the upper anchor further includes an external anti-rotational feature, and the manual fixture counter torque member further includes an internal anti-rotational feature for engaging the external anti-rotational feature of the upper anchor.

15. A distraction osteogenesis method, comprising the steps of:

forming a hole in a bone of a patient;

inserting a pre-assembled distraction osteogenesis fixture into the hole, the osteogenesis fixture comprising a lower anchor, a translation screw and an upper anchor, wherein the lower anchor includes an externally threaded portion, an anti-rotational feature, and a threaded internal passage, wherein the translational screw includes an externally threaded portion receivable by the threaded internal passage of the lower anchor, and wherein the upper anchor includes an internal passage for receiving a portion of the lower anchor and having an anti-rotational feature for engaging the anti-rotational feature of the lower anchor, the internal passage of the upper anchor including a surface for engaging the translational screw, at least a portion of the upper anchor being externally threaded;

cutting at least the cortical portion of the bone; and rotating the translational screw so as to cause linear translational movement of the upper anchor relative to the lower anchor, thereby distancing the bone surrounding the upper anchor from the bone surrounding the lower anchor.

16. The method according to claim 15, wherein the bone is a jawbone.

* * * * *